United States Patent [19]

Finucane et al.

[11] Patent Number: 5,770,251
[45] Date of Patent: Jun. 23, 1998

[54] PROCESS FOR ACCURATELY CONTROLLING MOISTURE OR SOLIDS LEVELS OF COMPOSITIONS WITH SMALL AMOUNTS OF OR NO SURFACTANT

[75] Inventors: Kevin Michael Finucane, Saddle Brook; Laurie Coyle, Park Ridge, both of N.J.

[73] Assignee: Lever Brothers Company, Division of Conopco, Inc, New York, N.Y.

[21] Appl. No.: 915,098

[22] Filed: Aug. 20, 1997

[51] Int. Cl.⁶ .................................................. G01N 33/00
[52] U.S. Cl. ........................... 426/231; 73/73; 73/863.81
[58] Field of Search ................................. 426/231; 73/73, 73/863.81; 324/307, 321

[56] References Cited

U.S. PATENT DOCUMENTS

| 3,966,973 | 6/1976 | Henry et al. | 426/231 |
| 5,487,843 | 1/1996 | Coyle et al. | 73/73 |
| 5,594,340 | 1/1997 | Coyle et al. | 73/863.84 |

FOREIGN PATENT DOCUMENTS 811124  3/1981  U.S.S.R. .

*Primary Examiner*—George Yeung
*Attorney, Agent, or Firm*—Ronald A. Koatz

[57] ABSTRACT

The present invention relates to a process for preparing compositions or slurries containing edible surfactants (generally at low levels) or no surfactants at all using an NMR sensor designed to measure water or solids content of the composition on-line.

1 Claim, 9 Drawing Sheets

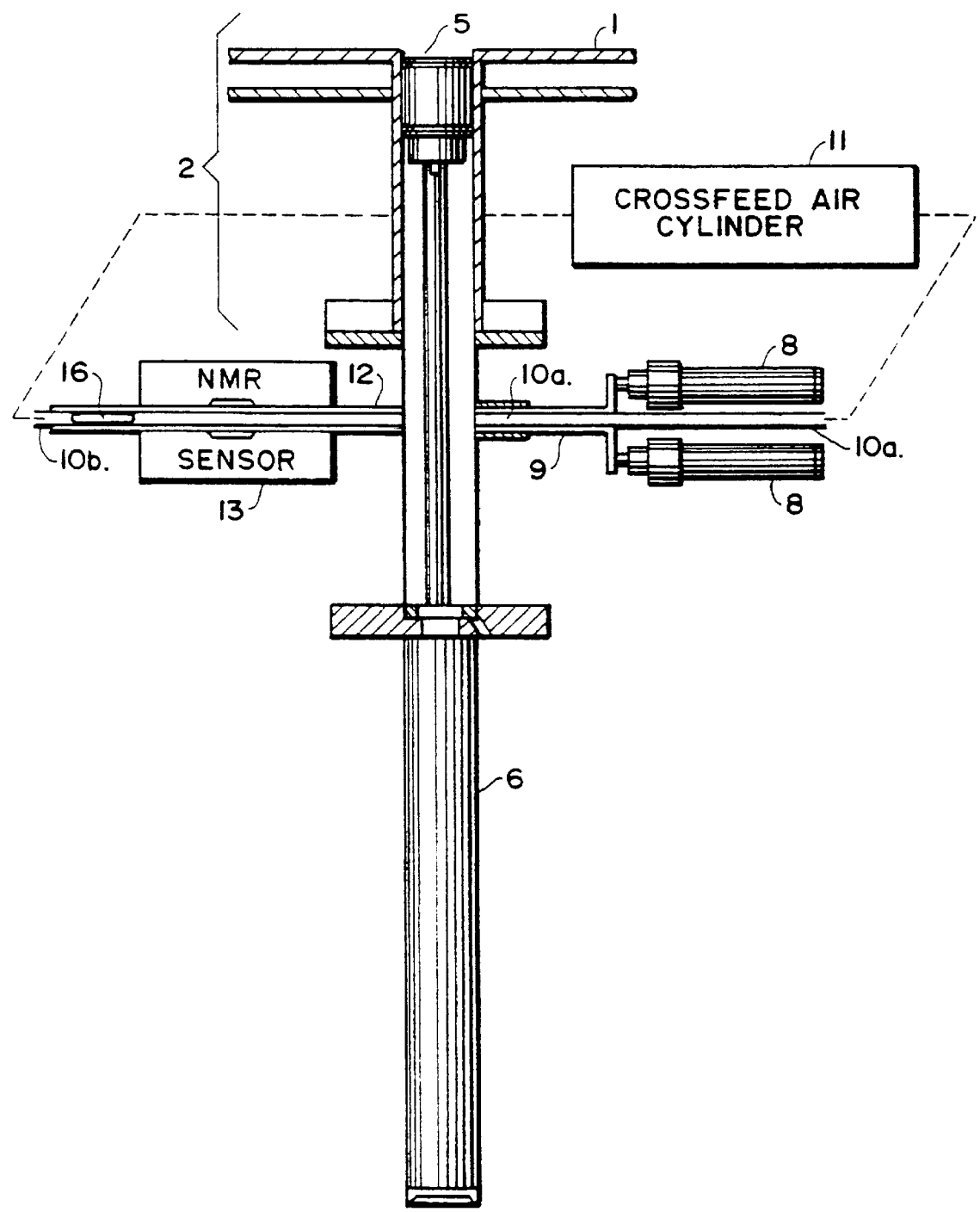

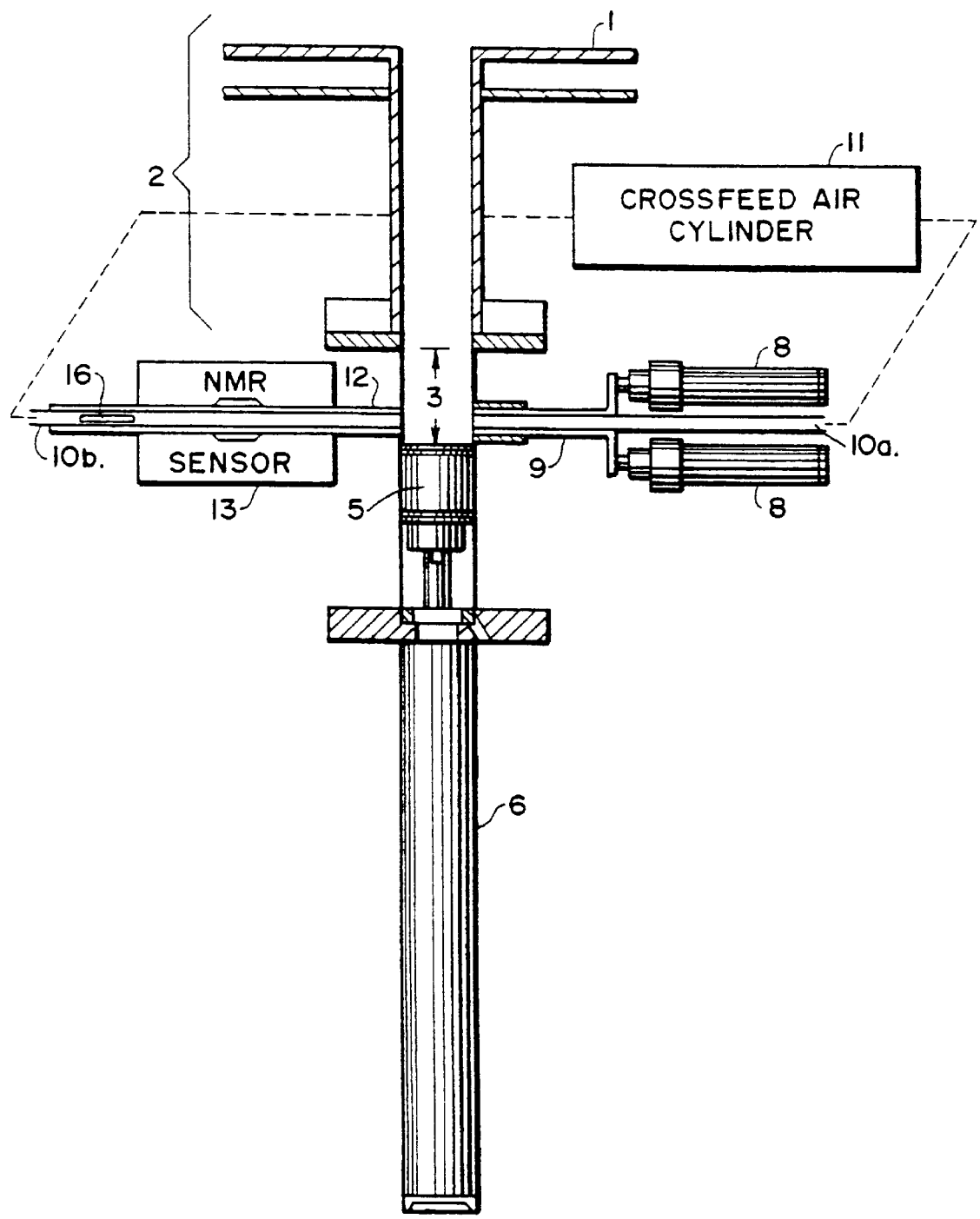

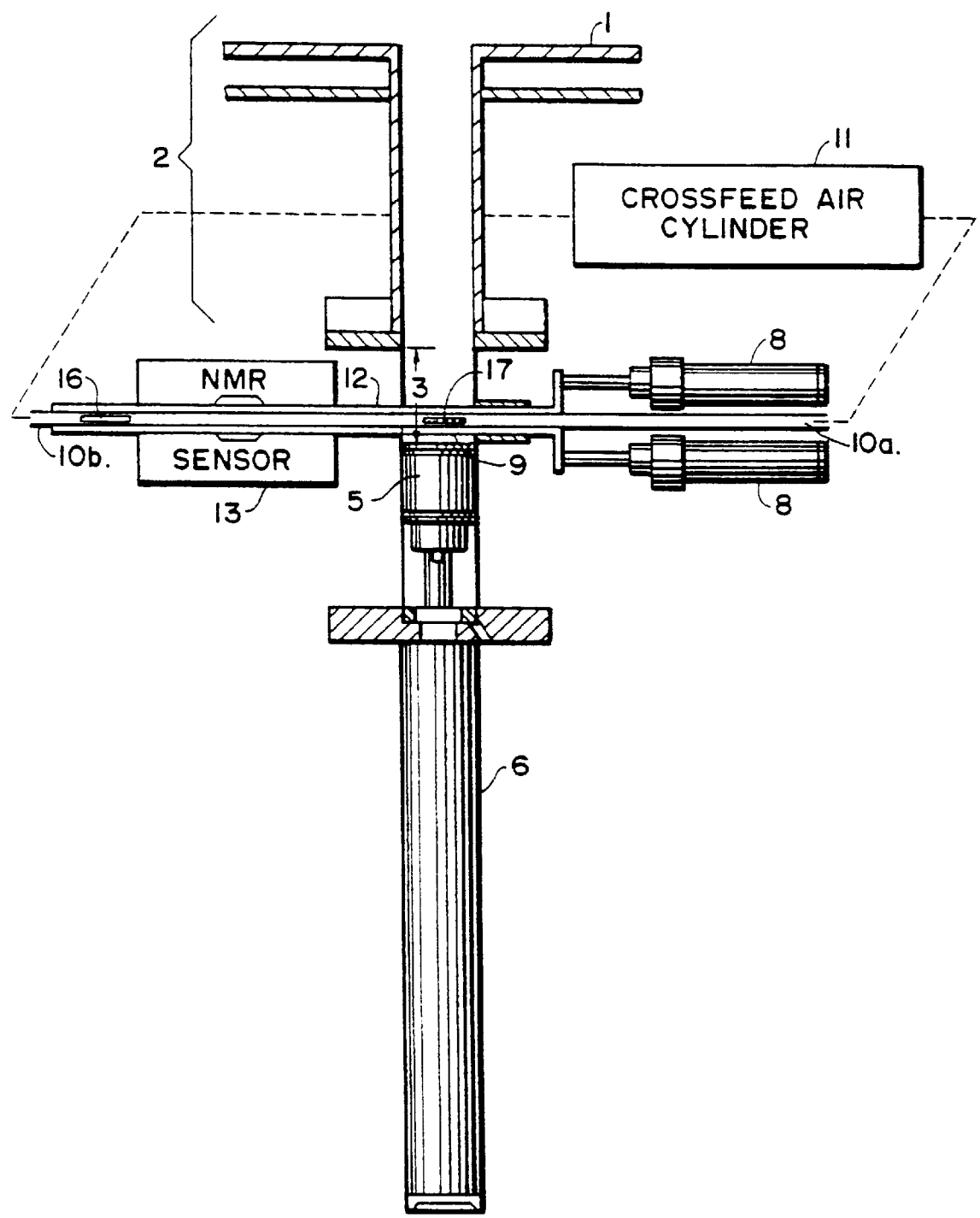

PROCESS FOR ACCURATELY CONTROLLING MOISTURE OR SOLIDS LEVELS OF COMPOSITIONS WITH SMALL AMOUNTS OF OR NO SURFACTANT

BACKGROUND OF THE INVENTION

The present invention relates to processes for accurately controlling moisture levels of compositions with small amounts of edible surfactant (e.g., foods) or no surfactants at all without having to stop the process to measure water or solids content (i.e., on line processing). In one embodiment the process is useful for controlling moisture content of food products such as biscuit and bread dough, batter (e.g., cake batter, pancake batter or biscuit batter); and non-flour foods such as apple sauce, peanut butter, chocolate, apple butter, jam, jelly, cooked mash potato, pudding, frosting, mayonnaise, soups (cooked soups and instant soups) and side dish sauces.

It is critical in the production of these products to add just the right amount of solids or water to obtain the desired moisture content.

One test previously used to obtain moisture measurements in low or non-surfactant compositions, particularly food product compositions, involved drying a small sample of product in a pan. These tests were time consuming, tedious and moreover did not produce instant results in a form required during processing to know exactly how much solid or water to add.

Other tests such as reflectance tests (dependent on surface characteristics of material) or conductance and dialectic tests have other drawbacks associated with accessibility and instantaneously measuring water or solids content.

Soviet Union Patent 811,124 discloses a method of controlling moisture in food samples. In this process, however, the samples must be weighed and then compared to a standard which must also be analyzed. This is not an on-line process.

U.S. Pat. No. 3,966,973 to Henry et al. (assigned to Pillsbury) relates in part to an NMR sensor device designed to address these issues. The NMR sensor in that invention is mounted to a pipe and differs significantly from NMR device used in the subject invention. First, unlike the present invention, the Henry device did not take samples off-line where they could be analyzed and then returned to pipe/batch mixer or ejected for calibration. Second, installation of the magnet in Henry is very expensive due to the size of the equipment. By contrast, the subject invention takes a small sample and passes it into the magnet region thereby minimizing cost.

The type of NMR device contemplated by the subject invention is taught in U.S. Pat. No. 5,594,340 to Coyle et al. (apparatus); and U.S. Pat. No. 5,487,843 to Coyle et al. (process for controlling moisture in detergent surfactant compositions).

In U.S. Pat. No. 5,487,843 to Coyle et al., however, the use of the apparatus was for compositions comprising 5% to 95% surfactant. It is not recited that the apparatus can be used in little (less than 5%, preferably 4% or less, more preferably 3% or less, most preferably 2% or less) or no surfactant compositions (e.g., minimal amounts of detergent surfactants are used in personal wash or fabric compositions among others), nor is it recited that the apparatus can be used specifically in food product or other non-detergent compositions.

As noted above, in food product (or other non-detergent) compositions, the closest art applicants are aware of is the Henry et al. patent wherein the sensor used is expensive (magnet or pipe) and does not teach or suggest the off-line sampling of the subject invention.

BRIEF DESCRIPTION OF THE INVENTION

Suddenly and unexpectedly, applicants have discovered that the apparatus of U.S. Pat. No. 5,599,340 and U.S. Pat. No. 5,487,843 can be used in compositions where surfactants are specifically edible surfactants as well as in compositions with no surfactant at all. Edible surfactants, when used, are generally used in lower amounts than surfactants in, for example, soap or detergent compositions. According to the invention, the level of edible surfactants in such food compositions (or solids contents of other materials in the food compositions) can be instantaneously determined and moisture or solids levels accurately controlled.

Specifically, the subject invention comprises both a process for preparing edible or no surfactant compositions as well as a method of determining and controlling moisture (or solids) in such compositions which generally have lower surfactant levels than soap or detergents.

In one embodiment, the invention comprises a process for preparing a composition having 0 to 30%, preferably 0.1 to 15%, preferably 0.1 to 10%, more preferably 0.1 to less than 5%, most preferably 0.1 to less than 3% edible surfactant, wherein said process comprises:

(i) mixing components comprising
  (a) 0 to less than 30% edible surfactant;
  (b) 1 to about 90% of a non-surfactant composition, preferably food product compositions; and
  (c) balance (up to 99%, preferably 1 to 90%) water
(ii) heating and/or mixing the component mixture;
(iii) removing a sample amount of the component mixture from a mixer or container while holding or processing the mixture, which sample amount is to be sampled by a device containing a nuclear magnetic resonance (NMR) sensor;
(iv) submitting the sample to an NMR sensor and measuring on-line NMR parameters of the sample and comparing the parameters to a preset calibration curve to obtain desired moisture levels; and repeating the NMR evaluation until the desired moisture level is obtained;
(v) releasing the mixture for further processing upon reaching desired moisture level.

In a second embodiment of the invention, the invention comprises determining and controlling the moisture in a low edible surfactant to no edible surfactant compositions (e.g., food product composition) using the process described above.

Specifically, moisture content of compositions of the invention can be controlled directly on line by utilizing an on line sampling device which samples small portions of the mixture (which may be viscous or non-viscous mixture having a viscosity from as low as 5 centipoise to as high as 1,000,000 centipoise) into a sensor unit (e.g., NMR sensor unit) and which sensor unit in turn calculates moisture values using nuclear magnetic resonance technology. The material is then returned by the sampling device to the process stream or vessel. Rather than put it back into the process stream, the same may be discharged for external analysis of moisture levels (e.g., to further calibrate the device).

Utilizing the information gathered from the sampled medium, the sensor can calculate instantly when the proper/desired moisture content has been reached so that the mixture can be released for additional processing (e.g., adding required solids or water). More specifically, the sensor measures NMR parameters of the sample and compares the parameters to a preset calibration curve to obtain desired moisture levels.

The apparatus allows material to be extracted for measurement from processes that are operating at normal ambient pressures and temperatures as well as from sealed vessels, operating under vacuum or pressure at elevated or depressed temperatures. It allows periodic collection of samples of very viscous or solid like materials which are measured using a relatively small, inexpensive sensor and associated apparatus to determine the moisture level. In addition, the apparatus may provide samples of the process material for external measurements and it returns all other material to the process vessel after each NMR measurement.

DESCRIPTION OF FIGURES

FIG. 4 also shows the sensor assembly 13, the sensor magnet 14, the sensor coil 15 and sample extraction port 16.

FIG. 5 is an end view showing the sampling device in the "clear position". The main piston 5 is fully extended and no product may enter the main collection cylinder 3. The facing ends of cross feed pistons 10a and 10b are located outside the inner bore of cylinder 3.

FIG. 6 shows the main piston 5 retracted, allowing the process material to flow into the main collection cylinder 3.

FIG. 7 shows the coring device 9 actuated to the left by cylinders 8 to form a core sample 17 that is located between the facing surfaces of cross feed pistons 10a and 10b.

DETAILED SUMMARY OF THE INVENTION

The present invention relates to an improved process for controlling levels of moisture or solids in compositions comprising low amounts of edible surfactants or no surfactant at all (e.g., preferably food compositions).

More particularly, the present invention relates to a process in which, while the ingredients forming the composition are mixed, the moisture content of the mixture can be efficiently and accurately determined to a desired level ±0.5% of target moisture levels, preferably±0.1%. This is in contrast to the previous methods of moisture control in which moisture is controlled by monitoring temperatures and levels of water evaporated (i.e., were not on-line) or by estimating moisture based on viscosity (i.e., were not accurate).

More specifically the invention provides a sampling instrument which extracts samples of compositions from a mixer or vessel being used to prepare the compositions (e.g., low to no surfactant compositions, preferably food compositions) and utilizes an NMR sensor built into the sampling device to evaluate moisture (or solids) content. Specifically, NMR parameters of the sample are measured and compared to a preset calibration curve to obtain desired moisture levels (i.e., NMR parameters are correlated to moisture levels). The samples may then either be returned into the mixer or processing stream or they may be removed from the sampling device altogether for external analysis of moisture levels. Utilizing this sampling device allows one to automatically analyze moisture content of the composition on line and thereby determine exactly when a desired moisture level is reached. In the preparation of chocolates, for example, when desired moisture levels are accurately met, the mixture is ready to be solidified (or not if it is intended to be a liquid) and sent downstream for further processing.

Figure 1:
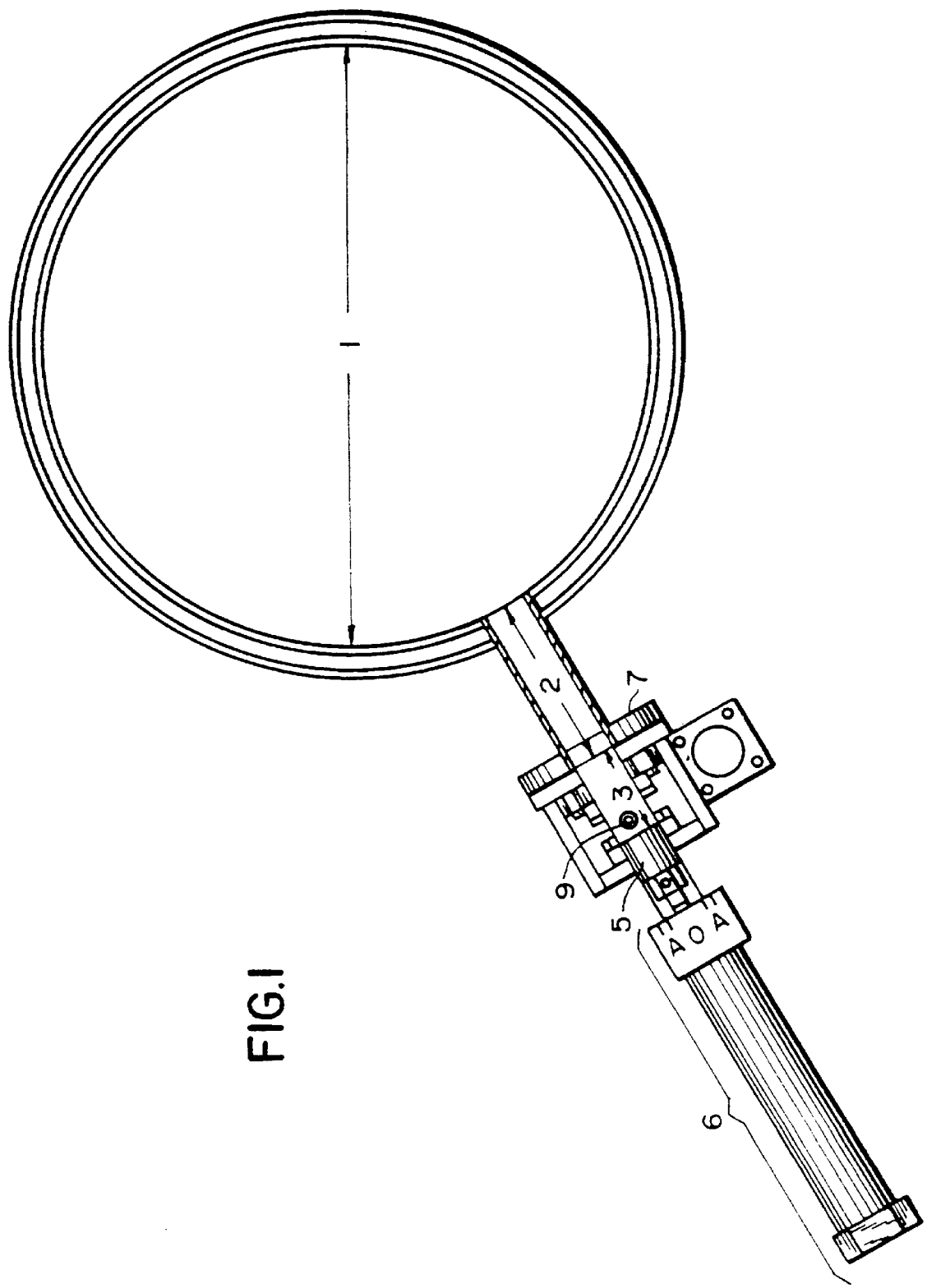
FIG. 1 is a side view of main piston 5 extracting sample from container 1 through pipe opening 2 into collection cylinder 3 from where a coring device 9 contained in a cross feed apparatus 4 (both seen in FIG. 2) will core a sample and a cross feed assembly piston 10a will feed the sample into a sensor 13 (also in FIG. 2).

Applicants refer now more particularly to FIG. 1, which represents a side view of the sampling device extracting sample from the mixer vessel or pipeline containing composition to be sampled. While the figures refer to extracting sample from this particular mixer or pipeline, it should be understood that the sampling device can be attached to the appropriate place for moisture or solids control in different compositions. Thus, if the moisture level of the aqueous slurry used to make composition needs to be controlled, the sample may be attached to, for example, the slurry tank or other suitable area.

Referring now to FIG. 1, a main piston 5 is found in a pipe opening 2 as close to the pipe as the connecting rod and piston in linear actuator 6 will allow (there is an opening in flange 7 which allows main piston 5 to go through the flange and be placed as close to pipe 1 as the linear range of actuator 6 will allow).

Main piston 5 is drawn backwards by pneumatic actuator 6 using air pressure applied to actuator 6 such that main piston 5 is brought back through pipe opening/extension 2. Piston 5 is drawn through the opening in flange 7 until it creates a main collection region in cylinder 3 where composition sample from pipe 1 will be drawn for measurement. Main piston 5 must be drawn far enough back so that it will sit behind the point where coring device 9 (seen more clearly in FIGS. 2 and 3) will be able to push through the diameter of the material in cylinder 3 to cut a sample which may be pushed into or through the NMR sensor.

Once the composition has been drawn into and through the opening 2 and the flange 7 into collection cylinder 3, a cross feed apparatus 4 (seen in more detail in FIGS. 2 and 3) is used to push or drive the composition from collection cylinder 3 into an NMR sensor 13 (see FIG. 2) where moisture content is measured and the sample is either returned to main collection cylinder 3 or drawn further back to an ejection port 16 for external sampling. If returned to collection cylinder 3, the linear actuator 6 can then use air pressure to push main piston 5 back through the opening in flange 7 and as far into pipe opening 2 as the travel range of actuator 6 will allow.

Figure 2:
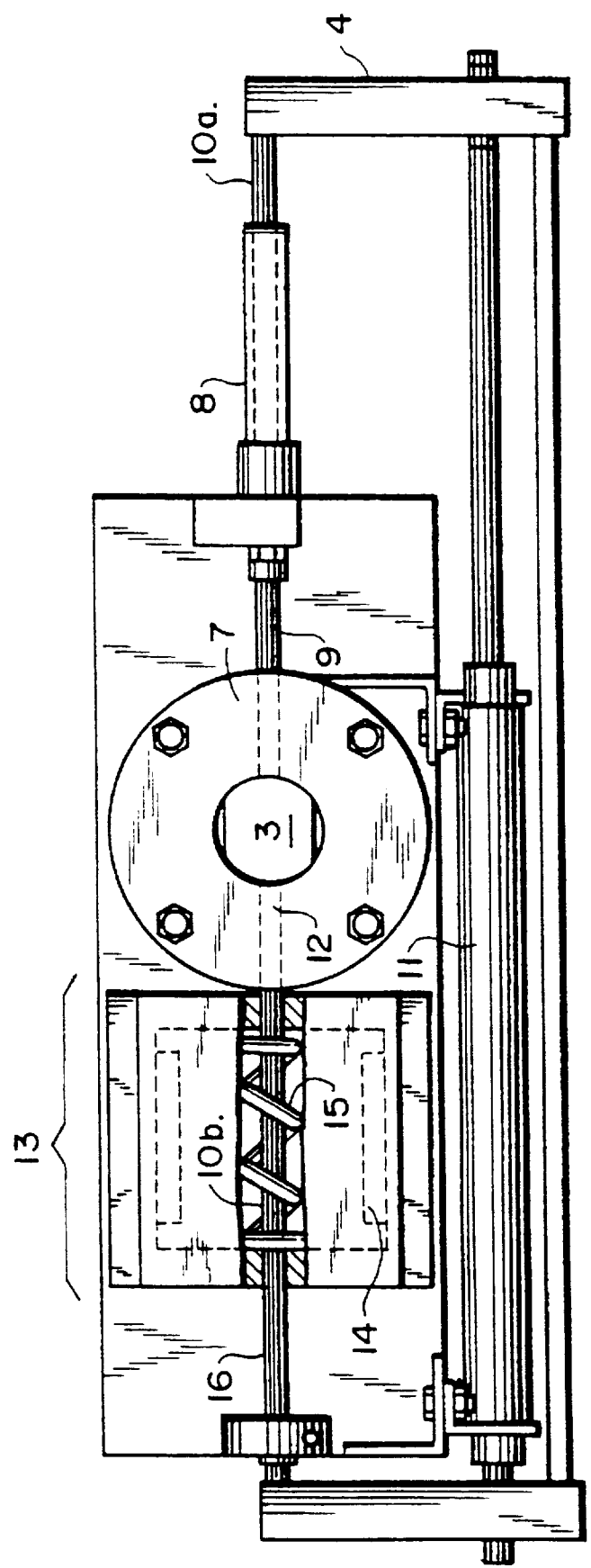
FIG. 2 is an end view of the coring device 9 and cross feed assembly piston 10a pushing the sample from collection cylinder 3 into the sensor assembly 13 for moisture evaluation.

Referring to FIG. 2 opening 3 is a view looking from pipe opening 2 into collection port 3 through the flange 7. 8 is the coring device air actuator which, when activated, pushes the coring device 9 through the main collection cylinder 3 and forms a sample. Cross feed assembly air actuator 11 is used to activate cross feed assembly piston 10a through coring device 9 thereby pushing the aforementioned sample into the NMR sensor 13. Sample is thereby pushed into the NMR sensor coil 15 located in NMR magnet 14.

After measuring moisture content, the composition sample may then be automatically returned to main collection cylinder 3 by cross feed assembly piston 10b or the sample may be further pushed into ejection port 16 by cross feed assembly piston 10a where it may be removed for external testing. This is required both to monitor accuracy of results as well as to allow the NMR sensor device to be accurately calibrated.

Figure 3:
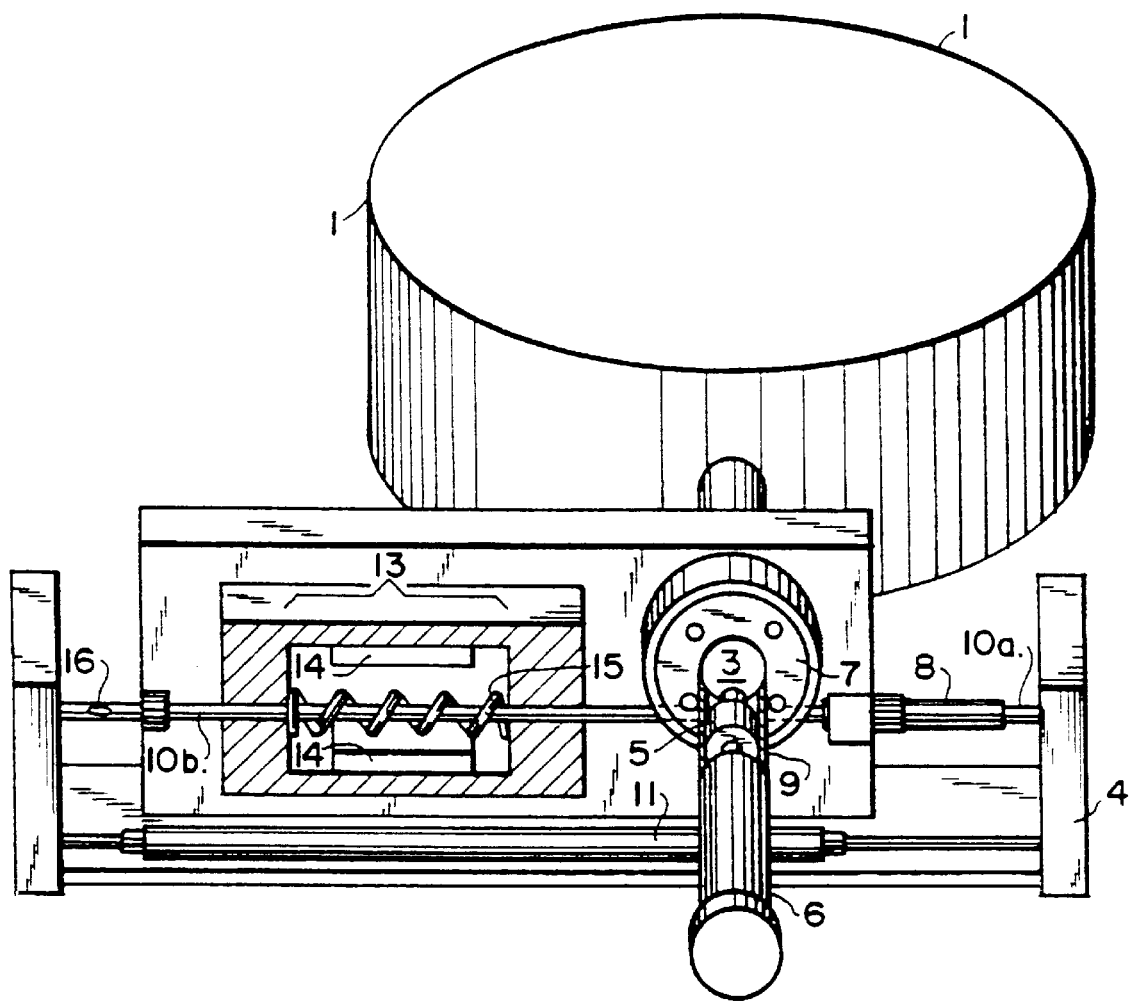
FIG. 3 is another end view similar to FIG. 2 but viewed from above and showing the positioning of the air cylinder 6, which moves main piston 5 in main collection cylinder 3.

FIG. 3 is another end view similar to FIG. 2 but viewed from above and showing the positioning of piston air actuator 6.

Referring to FIGS. 1, 2 and 3, the following is a description of how the sample is used:

(1) The main piston 5 in the fully extended position is retracted away from the mixer (process vessel etc.) and process material then flows into the main collection cylinder 3.

(2) the coring device 9 is actuated and slides to the left and diametrically through the process material collected in the main collection cylinder 3 independent of the cross feed assembly pistons 10a and 10b to form a core sample of the material.

(3) The cross feed assembly piston 10a is then actuated to the left so that it passes through the coring device 9, thereby pushing the core sample through the cross feed sample tube 12 and into the region surrounded by the radio frequency (RF) coil 15 in the NMR sensor 13.

(4) NMR readings are taken and the sample can be either: Extracted: The cross feed assembly piston 10a is then actuated further to the left, and the core sample is pushed through the ejection pod 16: or Returned to the mixer (process vessel, etc.): The cross feed assembly piston 10 is then actuated to the right and the sample is pushed by piston 10b back into the main collection cylinder 3: and The coring device 9 is then retracted, and the main piston 5 is returned to its fully extended position, thus returning the sample to the mixer 1.

Figure 4A:
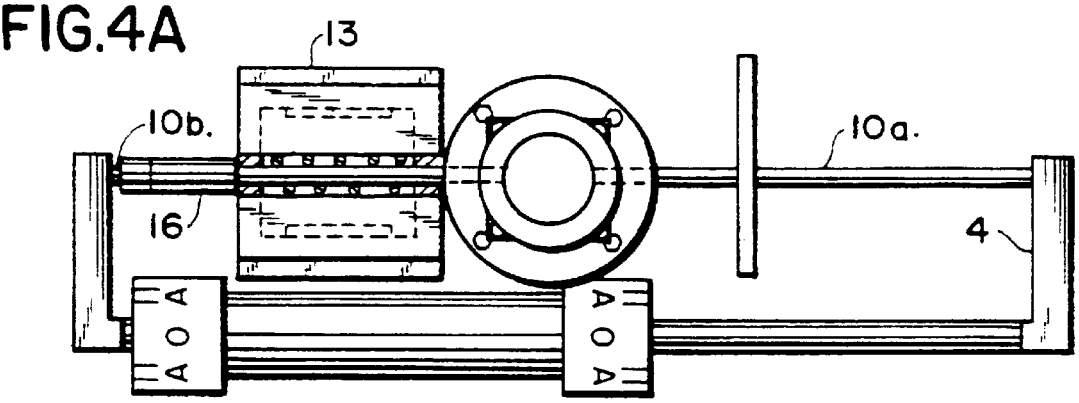
FIGS. 4A–4C are side views of sample being pushed into the NMR sensor 13 and of the sample being further extracted for external testing.

FIG. 4 is again an end view looking down from pipe opening 2 into main collection cylinder 3. In FIG. 4a the main collection port is assumed to be filled.

Figure 4B:
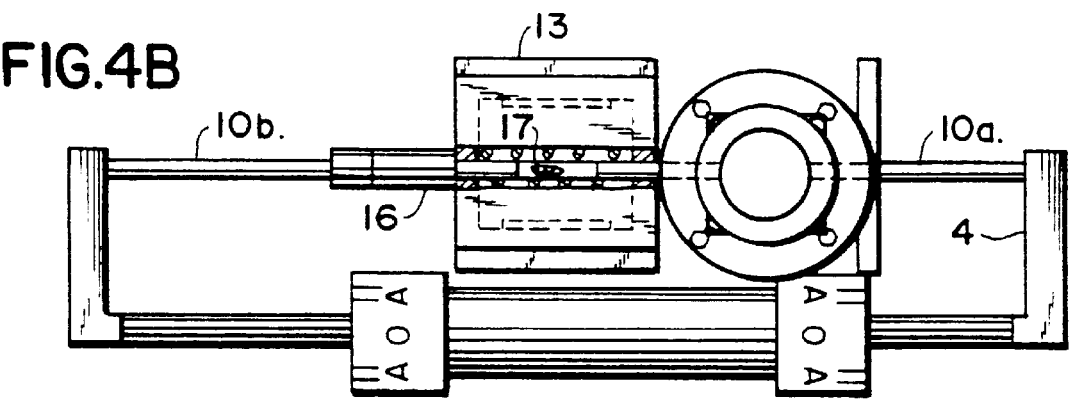
Figure 4C:
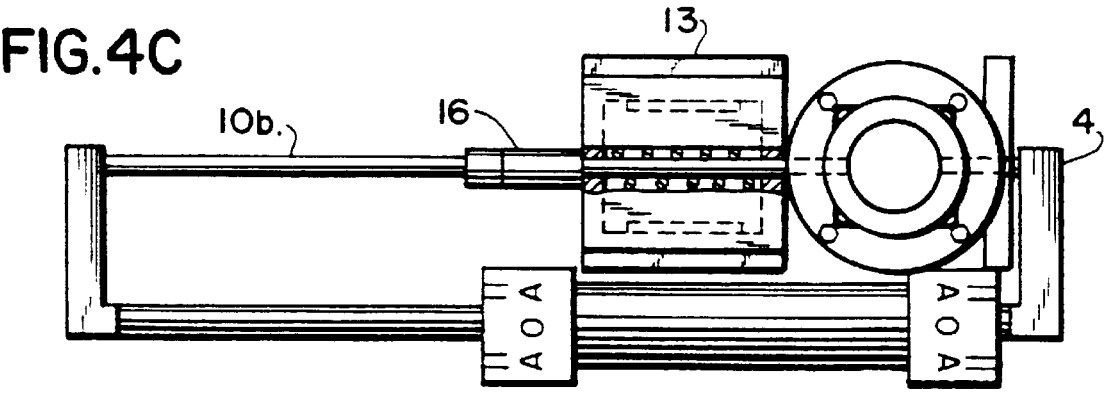
Figure 8:
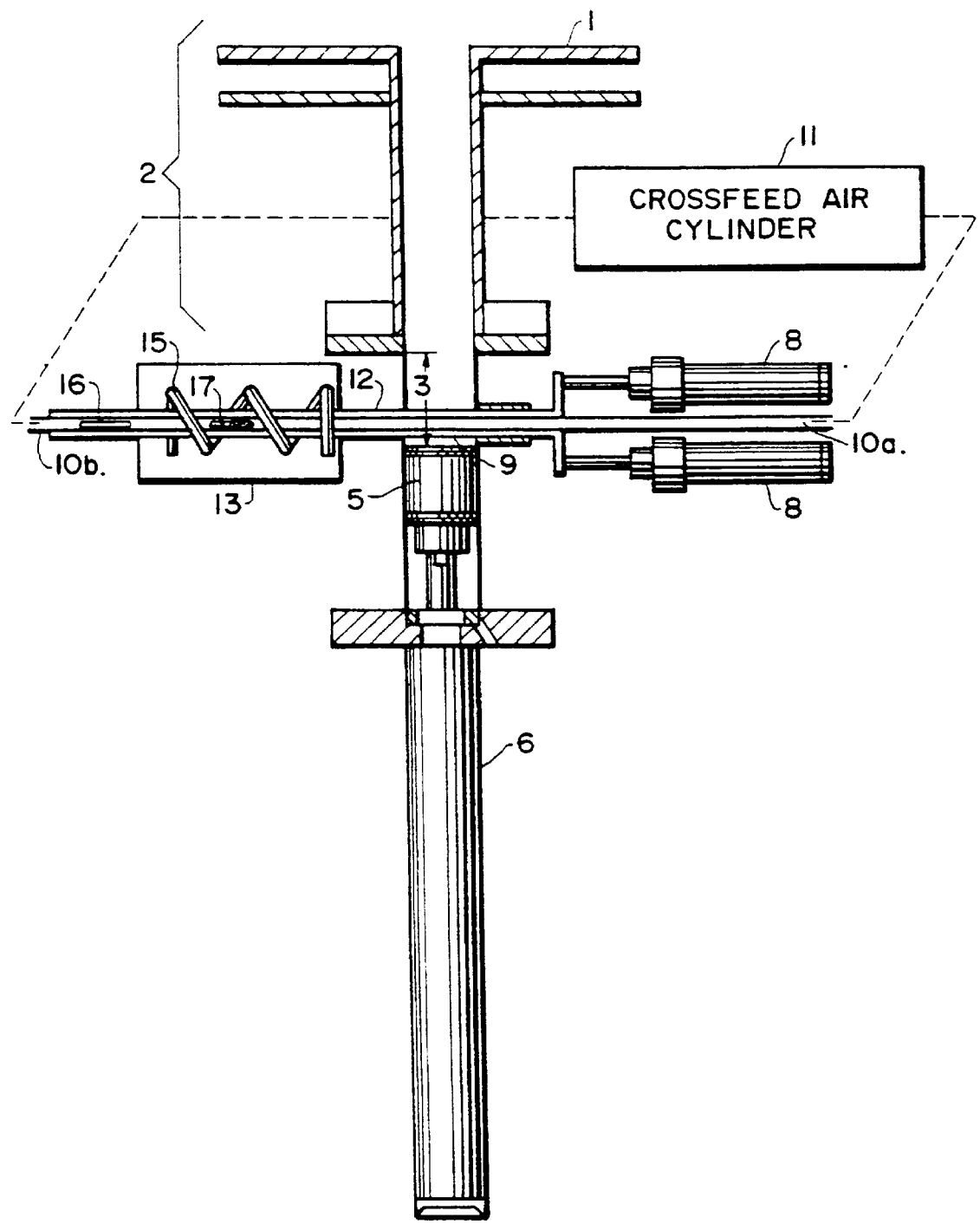
FIG. 8 shows the cross feed assembly piston 10a after it has been actuated by cylinder 11 to the left passing through the coring device 9 to push sample 17 into the NMR sensor coil 15.
Figure 9:
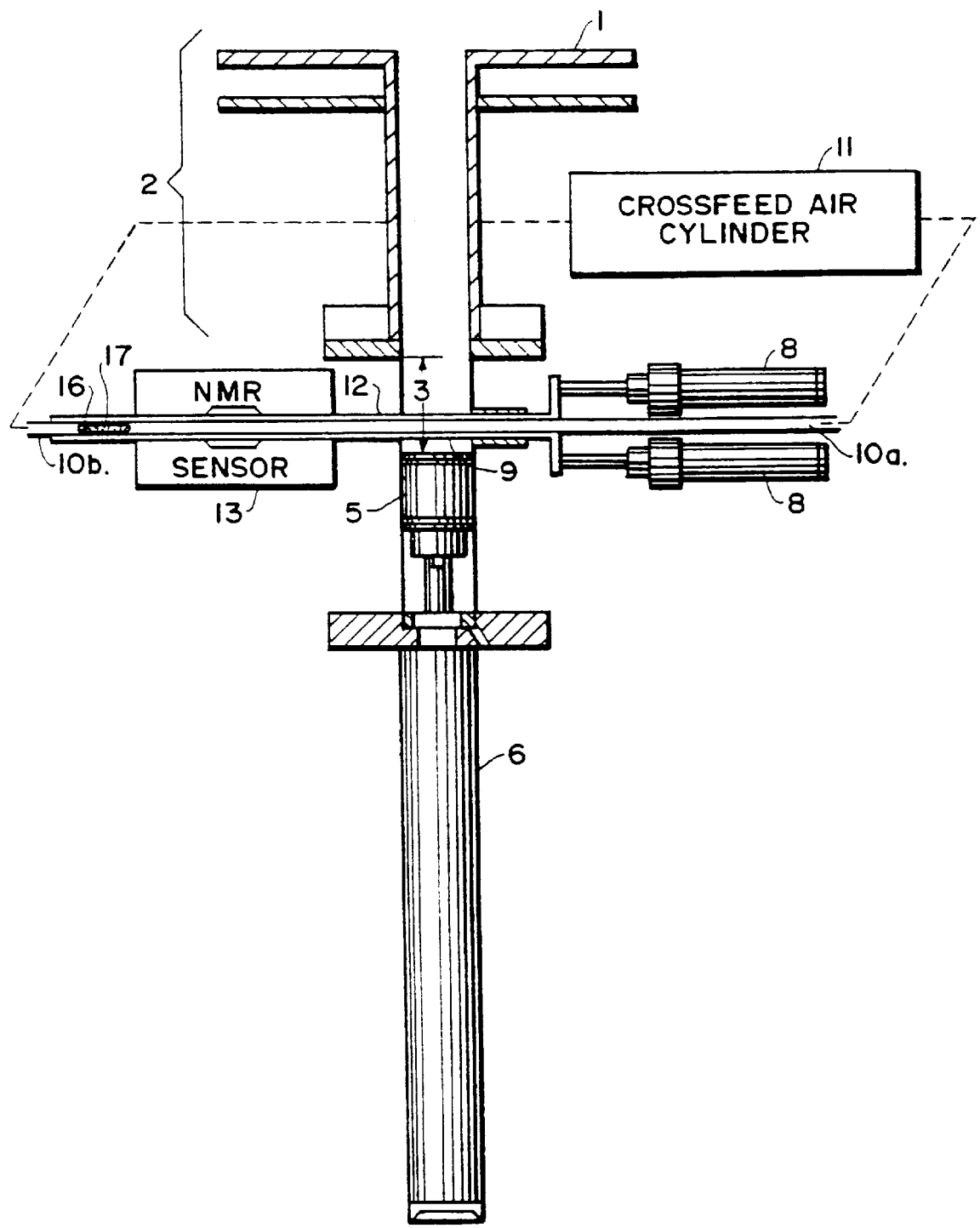
FIG. 9 shows the cross feed assembly piston 10a after it has been actuated all the way to the left and has pushed the sample 17 to the ejection port 16 where it can be removed from the sampling device. The sample 17 can be returned to the storage vessel if an external sample is not necessary. In order to return the sample to the storage vessel, the cross feed assembly piston 10b is actuated all the way to the right, the coring device 9 is retracted and then the main piston 5 is returned to its fully extended position.

FIG. 4b shows how cross feed assembly piston 10, actuated by piston 11, pushes a sample through the coring device into the NMR sensor region. The sample can be extracted from the sensor to provide external analysis (FIG. 4c).

Using the device of the invention, the moisture level of the sample is checked or compared to a preset desired moisture level (i.e., a preset calibration curve which correlates NMR parameters to desired moisture levels) and the sample is released for further processing when the desired level is obtained.

It should be noted that this invention is superior to any moisture controlling method used in the art in that no pre-weighing is required to determine moisture levels (e.g., as in the Karl-Fisher method or in the Soviet patent discussed above). Further, it is a very exact method for measuring water content on line as compared to other on-line methods which are much more inaccurate.

As noted above, the compositions of the invention can be any aqueous low or no surfactant mixture whether the aqueous surfactant mixture is used to make a final liquid product or whether it be used to make solid products.

Compositions

As noted, the compositions of the invention are compositions comprising low amounts of edible surfactant or no surfactant at all.

To the extent surfactants are used, they would be the type of surfactants associated specifically with the non-detergent compositions with which this application is concerned.

According to the present invention any edible surfactant maybe used although lipidic substances are preferred. However, the use of other, non lipidic surfactants, for example surfactant or amphophilic carbohydrates is not excluded. In general the preferred edible surfactants are selected from the group consisting of non-ionic surfactants, anionic surfactants and cationic surfactants.

Preferred nonionic surfactants are edible monoglycerides, diglycerides, polyglycerol esters, nonionic phospholipds, non-fatty carboxylic acid esters of fatty acid esters, partial sugar-fatty acids esters and, partial fatty acid esters of polyols and mixtures thereof.

Preferred cationic surfactants are cationic phospholipids, cationic non-fatty carboxylic acid esters of fatty acid esters and mixtures thereof.

Preferred anionic surfactants are lactylated fatty acid salts, anionic phospholipids, anionic non-fatty carboxylic acid esters of fatty acid esters and their metal salts, fatty acids and their metal salts and mixtures thereof.

The fatty acid chains used in these surfactants can be of any type and origin. Preferably, however $C_{8-28}$ fatty acid chains are present, more preferred $C_{12-22}$, for example $C_{14-18}$. The fatty acids may for example be saturated, unsaturated, fractionated or hydrogenated and be derived from natural (for example dairy, vegetable or animal) source or synthetic sources.

Preferably the total level of edible surfactants in the invention is from 0 to 30%, more preferred 0.1 to 15%, most preferred 0.1 to less than 5% by weight, preferably 4% or less of the composition.

One example of edible composition is a dressing or mayonnaise.

The level of edible surfactant material in the dressing will generally be from 0.1 to 15%, more preferred from 1 to 10%, most preferred from 2 to 8% by weight. Preferably the level of nonionic edible surfactant is from 0.1 to 15%, more preferred, 0.5 to 10%, most preferred 1 to 8% by weight. Especially preferred are monoglycerides as nonionic edible surfactants. Preferably the level of ionic edible surfactant is from 0 to 5%, more preferred 0.05 to 2%, most preferred 0.1 to 0.5% by weight.

In addition, dressings may contain one or more of other ingredients which may suitably be incorporated into dressings and/or mayonnaise. Examples of these materials are emulsifiers, for example egg yolk or derivatives thereof, stabilizers, acidifiers, biopolymers, for example hydrolyzed starches and/or gums or gelatin, bulking agents, flavors, coloring agents etc. The balance or the composition is water, which could advantageously be incorporated at levels of from 0.1 to 99.9%, more preferred 20 to 99%, most preferred 50 to 98% by weight.

Another possible embodiment includes spreads.

Spreads generally contain from less than 80% by weight of edible triglyceride materials. Suitable edible triglyceride materials are for example disclosed in Bailey's Industrial Oil and Fat Products, 1979. In spreads of non-reduced fat content (margarines), the level of triglyceride material will generally be more than 60% and less than 80%, preferably from 70 to 79% by weight. In spreads of reduced fat content the level of triglycerides will generally be from 30 to 60%, more general from 35 to 45% by weight. In very low fat spreads the level of triglycerides will generally be from 0 to 40%, for example 30%, 25%, 20% or even 10% or about 0%. Other fatty materials, for example sucrose fatty acid polyesters may be used as a replacement for part or all of the triglyceride material.

The edible surfactant material for use in spreads is preferably used at a level of from 0.1 to 15%, more preferred from 1 to 10%, most preferred from 2 to 8% by weight. Preferably the level of nonionic edible surfactant is from 0.1 to 15%, most preferred, 1 to 10%, most preferred, 2 to 8% by weight. Especially preferred are monoglycerides and lecithins as nonionic edible surfactants. Preferably the level of ionic edible surfactants from 0 to 5%, more preferred 0.05 to 2%, most preferred 0.1 to 0.5%. Preferred ionic edible surfactants are lactylated fatty acid salts and phophatidic acid.

In addition to the above mentioned ingredients, spreads in accordance to the invention may optionally contain further ingredients suitable for use in spreads. Example of these materials are gelling agents, sugar or other sweetener materials, EDTA, spices, salt, bulking agents, flavoring materials, coloring materials, proteins, acids etc. Particularly preferred is the incorporation of biopolymers in spreads. Suitable biopolymer materials are for example milk protein, gelatin, soy protein, xanthan gum, locust bean gum, hydrolyzed starches (for example Paselli SA2 and N-oil), and microcrystalline cellulose.

The amount of biopolymer in spreads of the invention is dependent on the desired degree of gelling and the presence of other ingredients in the composition. Usually the amount of gelling agent lies between 0 and 30%, mostly between 0.1 and 25% based on the weight of the aqueous phase of the spread. If hydrolyzed starches are present their level is preferably from 5 to 20%; other gelling agents are generally used at levels of up to 10%, mostly 1 to 7%, most preferred 2 to 5% all percentages being based on the weight of the aqueous phase. Particularly preferred are combination of say 5 to 15% hydrolyzed starch and 0.5 to 5% of other gelling materials. Preferably the other gelling material includes gelatin.

The balance of the composition is generally water, which may be incorporated at levels of up to 99.9% by weight, more general from 10 to 98%, preferably from 20 to 97% by weight. Spreads according to the invention may be fat and/or water continuous.

Another preferred embodiment of the invention is the use of mesomorphic phases of edible surfactants in whippable products, in particular whippable non-dairy creams, mousses, bavarois, etc. Preferred uses are as foam control agent and fat replacer.

Preferably the level of edible surfactant in whippable dairy products is from 0.1 to 30% by weight, more preferred 1 to 20%, most preferred 2 to 15% by weight of the composition. Preferably the edible surfactant material comprises nonionic surfactants such as monoglycerides, for example at levels of 0.1 to 30%, more preferred 1 to 20%, most preferred 2 to 15% by weight. In addition to the monoglyceride, co-surfactants may be present, for example at a level of 0 to 10%, more preferred 0.1 to 8%. A preferred cosurfactant is lecithin.

In addition to the edible surfactant materials, whippable products in accordance to the invention may advantageously contain other ingredients, for example proteins, sugar, emulsifiers, colorants, flavoring agents, fat (preferably vegetable fat), skimmed milk ingredients, biopolymers etc. For example the fat level may be less than 80%, more preferred 0 to 40%, for example about 5%, 15% or 30%. The balance of the composition is preferably water.

A further advantageous embodiment of the present invention relates to edible surfactants in frozen desserts. Suitable uses are as structuring agent, fat replacer, preservative, lubricating agent, consistency control agent, foaming agent, moisture retention agent and flavor release agent. Especially preferred is their use in frozen desserts of ice cream as a structuring agent, foaming agent, fat replacer or for improving melt-down properties.

Preferred frozen dessert compositions contain up to 10%, for example from 0.1 to 6% of edible surfactant, more preferred from 0.3 to 5%, most preferred from 0.5 to 2% by weight. Preferably the level of nonionic edible surfactants is up to 10%, for example from 0.5 to 5%, more preferred from 0.6 to 3%, most preferred from 0.8 to 1.5% by weight. Most preferred is the use of monoglycerides as the nonionic edible surfactant. Preferably the level of ionic edible surfactants is from 0 to 1%, more preferred 0.05 to 0.5% by weight. Preferred ionic edible surfactants are lactylated fatty acids.

In addition to edible surfactants, frozen desserts of the present invention may contain all conventional ingredients suitable for incorporation therein. For example, frozen desserts according to the present invention will usually contain one or more ingredients for improving the sweetness thereof. Preferably sugar is used as the sweetening material. If sugar is used as sweetening agent, the level thereof is preferably from 5 to 40%, more preferred 10 to 20%. If other sweetener materials such as for example aspartame (trademark) are used, the level of these materials is chosen such that the sweetness of the product resembles that of a product having the above mentioned sugar contents. Use of artificial sweetener materials may further require the use of one or more bulking agents, for example hydrogenated starch materials.

Furthermore frozen desserts according to the invention preferably contain milk solids fat (MSNF) at levels of 1 to 20%, more preferred 6 to 14% by weight. Additionally frozen desserts may advantageously contain low levels of emulsifier and/or stabilizing agents, for example at a level of 0 to 0.5%, more preferred 0.2 to 0.4% by weight. Optionally further ingredients suitable for incorporation in frozen desserts may be used, for example fruit, flavors, coloring agents, chocolate, nuts, preservatives, biopolymers and freezing point depressants. Generally the balance of the composition will be water.

Suitable recipes resulting in improved melt-down properties are for example as follows:

| | |
|---|---|
| 0.5–5% | monoglyceride, preferred 0.8–1.5% |
| 0–1% | ionic surfactant, preferred 0.05–0.5% |

-continued

| | |
|---|---|
| 10–20% | sugars, |
| 6–14% | milk solids non fat (msnf) |
| 0–0.5% | emulsifiers and stabilizer. |

The balance being water and usual additives for frozen desserts. In these recipes, usual, the sugars are contained both as sweeteners, freezing point depresssants and as texturizing agents. As usual these purposes may be achieved by different means, e.g., using sucrose next to invert sugar, fructose, glucose, maltodextrin, corn syrups. A preferred sugar combination in the above recipes being 5–8% maltodextrin and 9–14% sucrose.

The same applies to the milk solids non-fat: about one third thereof can be whey powder, so a suitable MSNF combination in the above recipes is 6–8% MSNF (including casein) and 1–3% whey powder.

Emulsifiers and stabilizers can be used as usual and examples thereof are widely known. Suitable amounts and products are exemplified in the examples A preferred range for the total amount of these additives is from 0.2 to 0.4%.

Frozen desserts according to the invention may be prepared by any conventional method for the preparation of ice-cream and the like.

The above are just a few non-limiting examples of compositions containing edible surfactants or no surfactant at all. Other non-limiting examples are described herein.

EXAMPLE 1

The following is an example of generic cooked soup composition which may be prepared using process of invention.

Ingredients in Approximate Order of Concentration

Corn Syrup Solids (25%–35%)
Salt (20%–38%)
Starch (12%–20%)
Vegetable Oil (hydrogenated) (1%–16%)
Yeast Extract (0%–8%)
Vegetable Powder (1–4%)
Animal Fat (if it is meat variety) (<5%)
Meat powder (if it is a meat variety) (<5%)
Spices/Flavors Although the above may apply to dry soups, the composition may also include 0 to 50% water if used for regular, non-dry soups.

EXAMPLE 2

The following is an example of an "Instant" soup (vegetable soup) which may be prepared:

Vegetable Powder (50%–80%)
Starch/Gum (4%–12%)
Salt (2%–8%)
Vegetable Fat (2%–7%)
Maltodextrin/Sugars (1%–7%)
Yeast Extract (1%–8%)
Spices/Flavors
Water (0–5%)

Again, the NMR of the invention may be used to control moisture or solids content in such compositions.

EXAMPLE 3

The following is example of creamy side dish sauce which may be prepared:

Dry dairy ingredients (Butter, Cheese, Cream, Whey, etc., depending upon flavor of variety (20%–60%)
Salt (6%–12%)
Starch (1%–18%)
Vegetable Fat (5%–12%)
Vegetable or Meat Powders (Depending upon variety) (3%–15%)
Flavors/Spices
Water (0–20%)

We claim:

1. A process for preparing an edible composition or slurry having edible surfactants or no surfactants comprising:

(i) mixing components comprising:
    (a) 0 to 30% edible surfactant;
    (b) 1% to 90% of non-surfactant ingredients other than water forming remainder of composition; and
    (c) balance water;

(ii) heating and/or mixing the component mixture:

(iii) removing a sample amount of the component mixture from a mixer pipeline or container while holding or processing the mixture, which sample amount is to be sampled by a device containing a nuclear magnetic resonance (NMR) sensor;

(iv) submitting the sample to an NMR sensor and measuring on-line NMR parameters of the sample and comparing the parameters to a preset calibration curve to obtain desired moisture or solids levels; and repeating the NMR evaluation until the desired moisture or solids level is obtained;

(v) releasing the mixture for further processing upon reaching desired moisture or solids level.

* * * * *